(12) United States Patent
Yamada et al.

(10) Patent No.: US 7,329,251 B2
(45) Date of Patent: Feb. 12, 2008

(54) LASER TREATMENT APPARATUS

(75) Inventors: Tsuyoshi Yamada, Toyota (JP);
Kenichi Hayashi, Gamagori (JP);
Yasuyuki Naito, Nukata-gun (JP); Seiki Tomita, Gamagori (JP)

(73) Assignee: Nidek Co., Ltd., Gamagori-shi (JP)

( * ) Notice: Subject to any disclaimer, the term of this patent is extended or adjusted under 35 U.S.C. 154(b) by 0 days.

(21) Appl. No.: 11/016,960

(22) Filed: Dec. 21, 2004

(65) Prior Publication Data

US 2005/0143720 A1 Jun. 30, 2005

(30) Foreign Application Priority Data

Dec. 25, 2003 (JP) ............................. 2003-429114

(51) Int. Cl.
*H01S 3/10* (2006.01)
*A61B 18/20* (2006.01)
*A61F 9/08* (2006.01)

(52) U.S. Cl. ............................. 606/4; 372/38.1; 606/3; 606/10

(58) Field of Classification Search ............... 606/4–6; 372/38.1

See application file for complete search history.

(56) References Cited

U.S. PATENT DOCUMENTS

| | | | | |
|---|---|---|---|---|
| 4,951,663 A | * | 8/1990 | L'Esperance, Jr. ............ 607/89 |
| 5,123,007 A | * | 6/1992 | Miyauchi et al. ............ 369/100 |
| 5,151,909 A | * | 9/1992 | Davenport et al. ........... 372/22 |
| 5,229,591 A | * | 7/1993 | Heiman et al. ......... 235/462.25 |
| 5,309,461 A | * | 5/1994 | Call et al. ................. 372/38.09 |
| 5,353,146 A | * | 10/1994 | Webb .......................... 398/175 |
| 5,502,298 A | * | 3/1996 | Geller ......................... 250/205 |
| 6,066,127 A | * | 5/2000 | Abe .............................. 606/2 |
| 6,585,722 B1 | * | 7/2003 | Abe .............................. 606/4 |
| 6,636,537 B2 | | 10/2003 | Takada |
| 2003/0149425 A1 | | 8/2003 | Takada et al. |

* cited by examiner

*Primary Examiner*—Henry M. Johnson, III
(74) *Attorney, Agent, or Firm*—Oliff & Berridge, PLC

(57) ABSTRACT

A laser treatment apparatus for performing treatment by irradiating an affected part with a laser beam comprises: a laser source capable of emitting beams of a plurality of different wavelengths; a first setting unit which sets an irradiation amount of a laser beam for treatment of a wavelength to be used for treatment; an emission amount changing unit which changes an emission amount of the beam in plural levels; an attenuating unit which attenuates the beam emitted by the laser source; and a control part which controls the emission amount changing unit and the attenuating unit based on the set irradiation amount of the treatment beam.

4 Claims, 9 Drawing Sheets

LASER TREATMENT APPARATUS

BACKGROUND OF THE INVENTION

1. Field of the Invention

The present invention relates to a laser treatment apparatus for performing treatment by irradiating an affected part with a laser beam.

2. Description of Related Art

There has been proposed a laser source (a laser oscillator) of a laser treatment apparatus that uses a solid-state laser medium such as an Nd:YAG crystal, and a wavelength converter (a wavelength converting element) such as a nonlinear crystal, and is capable of emitting (oscillating) treatment laser beams of a plurality of different wavelengths (colors) in a visible region. Such laser source includes resonance optical systems for emitting the treatment laser beams of different wavelengths (see U.S. Pat. No. 6,636,537 corresponding to Japanese unexamined patent publication 2002-151774).

As a control system for driving a laser source, commonly used is a so-called "power on-demand" system in which a necessary amount of electric current is applied to the laser source only when needed and the laser source emits an amount of a laser beam required to irradiate a needed amount of the laser beam to an affected part. In the laser source including the resonance optical systems for emitting laser beams of different wavelengths, each resonance optical system has to be adjusted to stably provide the emission amount of a laser beam of every wavelength needed for treatment. The emission amount of a laser beam of a certain wavelength from such laser source can be proportional in one-one relation to the amount of applied electric current, whereas the emission amount of a laser beam of another wavelength is not proportional in one-one relation to the amount of applied electric current as shown in FIG. 8. For this reason, the laser treatment apparatus having such laser source cannot adopt the power on-demand system.

As a measure corresponding to above, it is conceivable that the emission amount of a laser beam by the laser source is set to be consistently constant and further the irradiation amount of the laser beam is controlled by use of an attenuating means such as a polarization member or a ½ wave member. If the emission amount of the laser beam is set to be consistently constant, however, it is likely to place a load on optical elements disposed in the resonance optical systems and the laser source. This may shorten their useful lives.

SUMMARY OF THE INVENTION

The present invention has been made in view of the above circumstances and has an object to overcome the above problems and to provide a laser treatment apparatus capable of stably controlling an irradiation amount of a treatment laser beam.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided a laser treatment apparatus for performing treatment by irradiating an affected part with a laser beam, the apparatus comprising: a laser source capable of emitting beams of a plurality of different wavelengths; a first setting unit which sets an irradiation amount of a laser beam for treatment of a wavelength to be used for treatment; an emission amount changing unit which changes an emission amount of the beam in plural levels; an attenuating unit which attenuates the beam emitted by the laser source; and a control part which controls the emission amount changing unit and the attenuating unit based on the set irradiation amount of the treatment beam.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
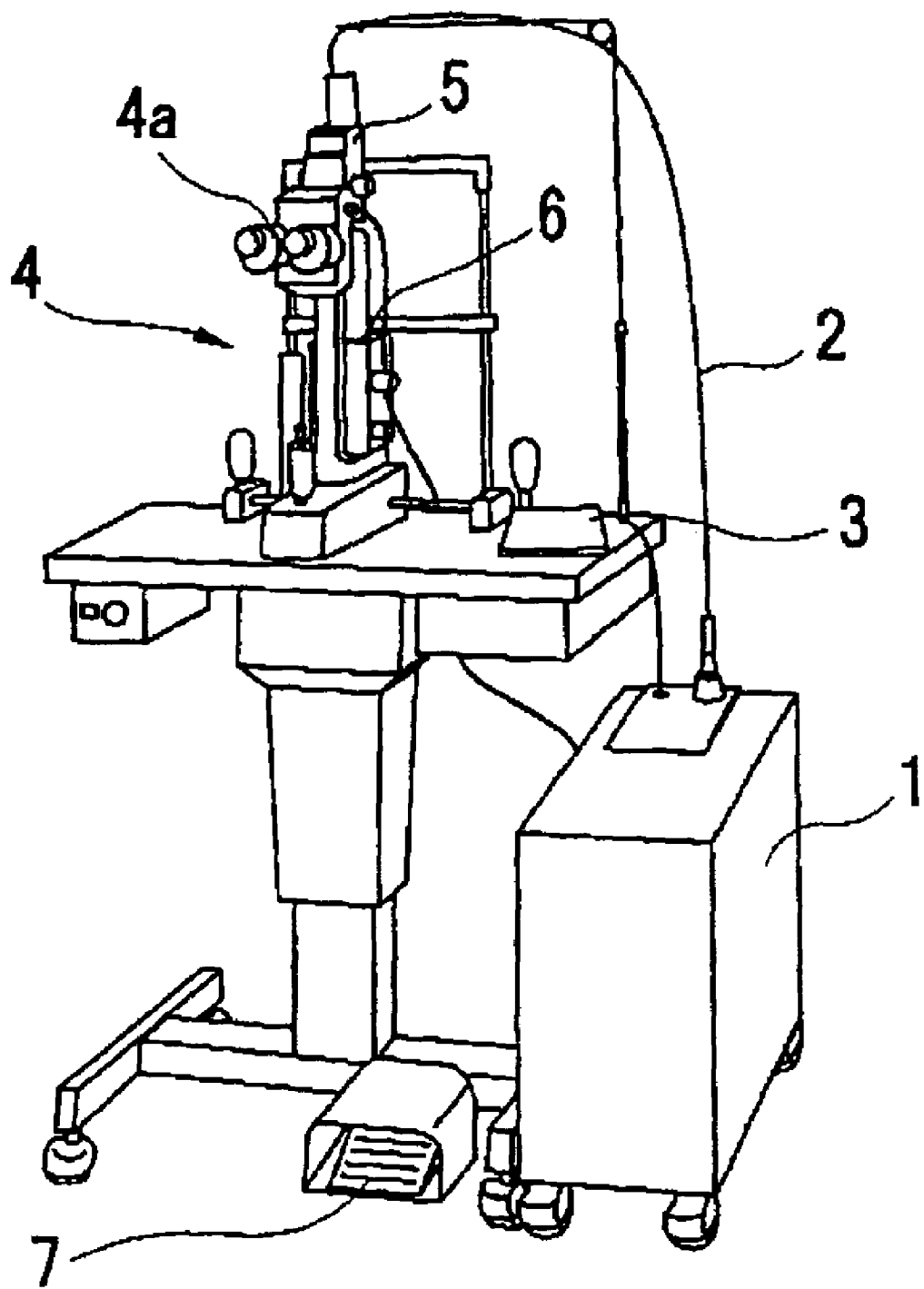
FIG. 1 is a schematic perspective view of a laser treatment apparatus.

A detailed description of a preferred embodiment of a laser treatment apparatus embodying the present invention will now be given referring to the accompanying drawings. FIG. 1 is a schematic perspective view of a laser photocoagulation treatment apparatus. A main unit 1 of the apparatus contains a laser source mentioned later, an optical system which delivers a treatment laser beam (hereinafter, a "treatment beam") emitted by the laser source into an optical fiber 2, and other components. A control box 3 is used, for example, for setting treatment conditions (irradiation conditions) such as a wavelength (a color), an irradiation amount, irradiation time (duration) of the treatment beam and displaying each set value and further for selecting an operation mode of the apparatus and displaying the selected mode. A slit lamp delivery 4 is used for irradiating the treatment beam to an affected part of a patient's eye while allowing an operator to observe the patient's eye. This slit lamp delivery 4 includes an irradiation part 5 for irradiating the treatment beam having been delivered thereto through the optical fiber 2, an illumination part 6 for illuminating the patient's eye, a binocular microscopic part 4a for allowing the operator to observe the patient's eye, and other components. A footswitch 7 is used for generating a trigger signal to command irradiation of the treatment beam.

Figure 2:
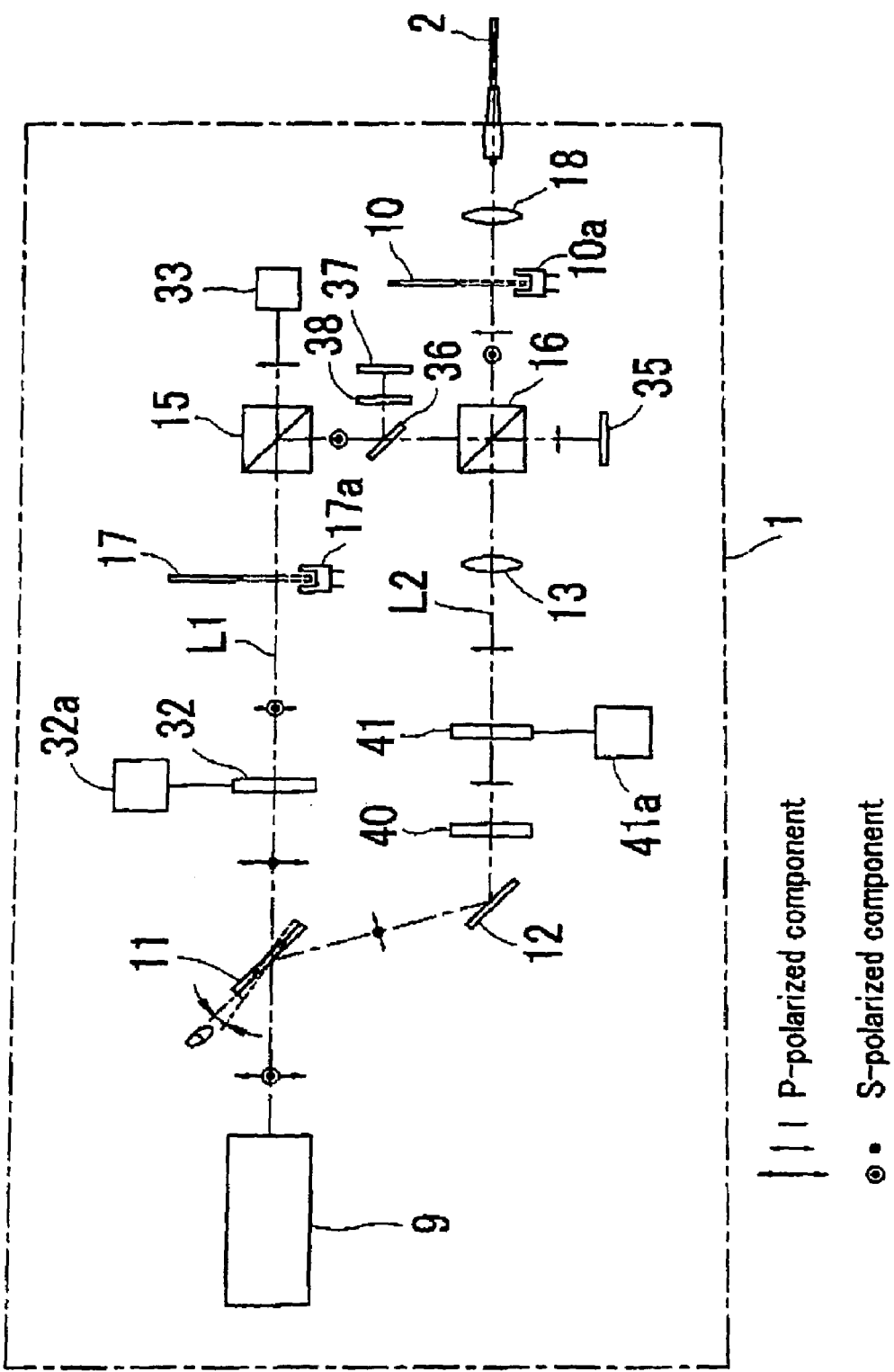
FIG. 2 is a schematic structural view of an optical system in the apparatus.
Figure 4:
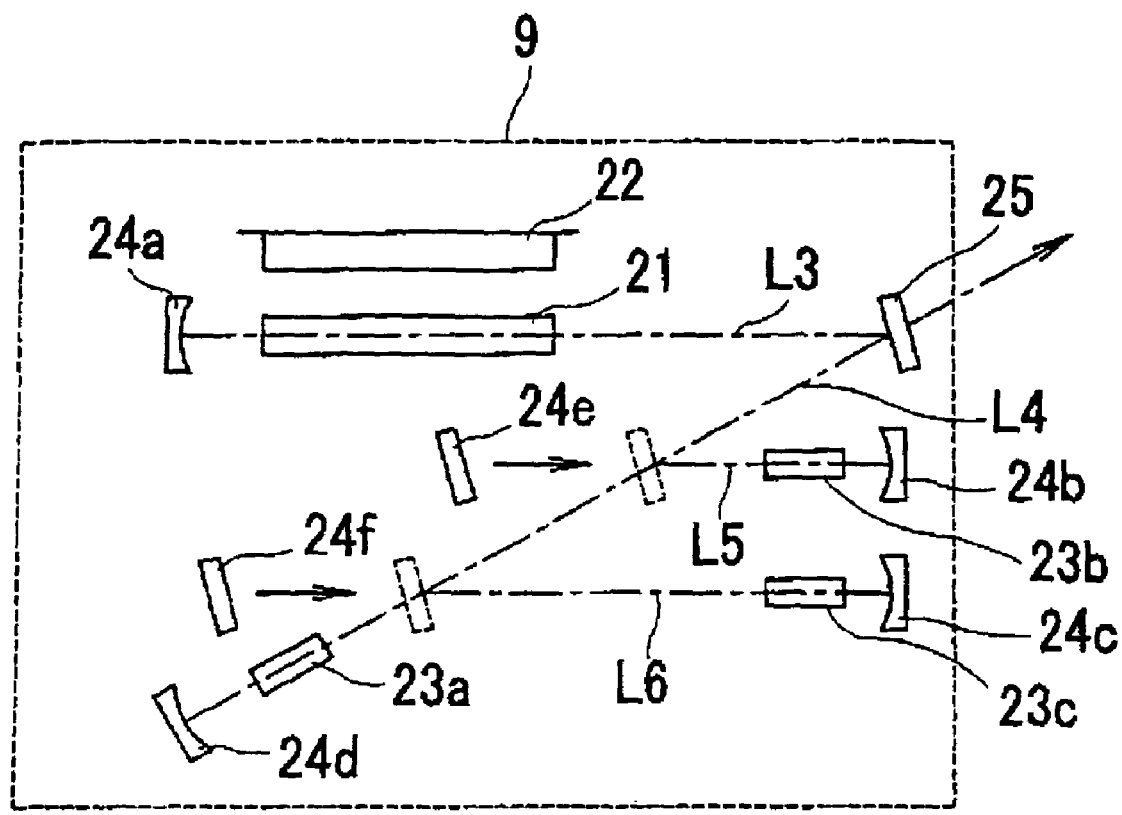
FIG. 4 is a schematic structural view of an optical system in a laser source.

FIG. 2 is a schematic structural view of an optical system provided in the main unit 1. The laser source 9 is, as shown in FIG. 4, internally provided with an Nd:YAG crystal 21 (hereinafter, referred to as "rod") which is a solid-state laser medium, a laser diode 22 (hereinafter, referred to as "LD") serving as an exciting light source, nonlinear crystals 23a, 23b, and 23c (hereinafter, referred to as "NLC") serving as wavelength converters (wavelength converting elements), total reflection mirrors (high reflectors) 24a to 24f (hereinafter, referred to as "HR"), and an output mirror 25. A well known crystal is used as the LD 22.

The Nd:YAG crystal emits light having a plurality of oscillation lines (peak wavelengths) in a near infrared region by exciting light from the exciting light source. Therefore, the apparatus in the present embodiment is constructed such that each second harmonic light of three oscillation lines; about 1064 nm, about 1123 nm, and about 1319 nm, which are wavelengths with high power among the plural oscillation lines emitted from the above crystal, is generated with the use of the nonlinear crystal, thereby emitting (oscillating) laser beams of three colors with wavelengths of about 532 nm (green), about 561 nm (yellow), and about 659 nm (red), respectively. The wording "about" will be omitted in the following description.

On the optical path of an optical axis L3 on which the rod 21 is placed, an HR 24a is disposed at one end thereof, and the output mirror 25 is arranged at a predetermined inclination angle at the other end. The HR 24a in the present embodiment has the property of totally reflecting the light (beams) of wavelengths of 1064 to 1319 nm. The output mirror 25 in the present embodiment has the property of totally reflecting the light (beams) of wavelengths of 1064 to 1319 nm, while transmitting the light (beams) of wavelengths of 632 to 659 nm.

On the optical path of an optical axis L4 in a reflecting direction of the output mirror 25, an NLC 23a and an HR 24d are fixedly disposed. The NLC 23a is placed so as to generate the light (beam) of 659 nm which is the second harmonic light (beam) from the light (beam) of 1319 nm. The HR 24d has the property of totally reflecting the light (beam) of 1319 nm and the light (beam) of 659 nm. This optical arrangement constructs a first resonance optical system in which the HR 24a and the HR 24d constitute a resonator in a pair in which the rod 21, the output mirror 25, and the NLC 23a are interposed between them. Thus, the light (beam) of 659 nm generated by the NLC 23a can be emitted through the output mirror 25.

An HR 24e is disposed to be movable onto/off from the optical path of the optical axis L4 between the output mirror 25 and the NLC 23a. This HR 24e has the property of totally reflecting the light (beam) of 1064 nm and the light (beam) of 532 nm. On the optical path of an optical axis L5 in a reflecting direction of the HR 24e, an NLC 23b and an HR 24b are fixedly disposed. The NLC 23b is placed so as to generate the light (beam) of 532 nm which is the second harmonic light (beam) from the light (beam) of 1064 nm. The HR 24b has, as with the HR 24e, the property of totally reflecting the light (beam) of 1064 nm and the light (beam) of 532 nm. In this optical arrangement, when the HR 24e is moved onto the optical path of the optical axis L4, the HR 24a, the rod 21, and the output mirror 25 of the first resonance optical system also serves to construct a second resonance optical system in which the HR 24a and the HR 24b constitute a resonator in a pair in which the rod 21, the output mirror 25, and the NLC 23b are interposed between them. Thus, the light (beam) of 532 nm generated by the NLC 23b can be emitted through the output mirror 25.

The beam splitter 11 is for example a transparent glass plate (a refractive index of about 1.5 in the present embodiment) which splits a beam emitted by the laser source 9 at a predetermined ratio. This beam splitter 11 is arranged so that an incident angle of a beam which enters the beam splitter 11 is 52°, deviated by an angle θ of 43° from a Brewster angle (56.3°). Due to this arrangement, the beam splitter 11 allows about 99.9% (in the present embodiment) to about 99.5% of a P-polarized component of the beam to pass through it, while reflecting about 0.1% (in the present embodiment) to about 0.5% of the P-polarized component. The beam splitter 11 also allows about 80% of an S-polarized component of the beam to pass through it, while reflecting about 20% of the S-polarized component. Thus, about 1/1000 (in the present embodiment) to about 5/1000 of the P-polarized component can be taken out from the beam when reflected by the beam splitter 11. Hereinafter, the wording "about" will be omitted.

99.9% of the P-polarized component and 80% of the S-polarized component having passed through the beam splitter 11 travel along the optical path of an optical axis L1 and then enter a ½ wave member. 32 disposed on the optical path of the optical a L1.

A shutter 17 for the treatment beam is disposed on the optical path of the optical axis L1. This shutter 17 is inserted in the optical path by driving of an inserting/removing unit 67 (see FIG. 3) to intercept the beam when the treatment beam is not required. The opening and closing (insertion and removal) of the shutter 17 is detected by a shutter sensor 17a.

On the optical path of the optical axis L1, further, there is disposed a beam splitter 15 which splits the beam by allowing the P-polarized component to pass through it while reflecting the S-polarized component. The P-polarized component having passed through the beam splitter 15 enters a diffuser 33. By a rotation angle of the ½ wave member 32 which is rotated by driving of a rotating unit 32a and the beam splitter 15, the amount of the S-polarized component to be reflected by the beam splitter 15 is changed, thereby controlling the irradiation amount of the treatment beam.

On the optical path of the optical axis L1 in a reflecting direction of the beam splitter 15, there are disposed a beam splitter 36 which reflects part of the S-polarized component, while allowing the rest to pass through it, and a beam combiner 16 which reflects the S-polarized component having passed through the beam splitter 36 while allowing the P-polarized component having traveled along the optical path of an optical axis L2 mentioned later, thus combining those components. On the optical path in a reflecting direction of the beam splitter 36, a filter 38 which blocks the P-polarized component and an output sensor 37 are disposed. The filter 38 is disposed in a polarizing direction to allow almost all the S-polarized component while blocking almost all the P-polarized component. The output sensor 37 detects the S-polarized component having passed through the filter 38. The output (power) of the treatment beam is thus detected, i.e., monitored.

0.1% of the P-polarized component and 20% of the S-polarized component having been reflected by the beam splitter 11, are reflected by the mirror 12, travel along the optical path of the optical axis L2, and then enter a filter 40 disposed on the optical path of the optical axis L2. The filter 40 is disposed in a polarizing direction to allow almost all the P-polarized component while blocking almost all the S-polarized component. The P-polarized component having passed through the filter 40 enters a polarizing member 41 disposed on the optical path of the optical axis L2. By a rotation angle of the polarizing member 41 which is rotated by driving of a rotating unit 41a, the amount of the P-polarized component allowed to pass through the polarizing member 41 is changed, thereby controlling the irradiation amount of the aiming beam. A compensating lens 13 is disposed on the optical path of the optical axis L2, which compensates for a difference in optical length between the optical axes L1 and L2.

Almost all the P-polarized component having passed through the polarizing member 41 is allowed to pass through the beam combiner 16 and combined with the S-polarized component having passed through the optical path of the optical axis L1. Part of the P-polarized component (about 10%) is reflected by the beam combiner 16 toward an output sensor 35. The output sensor 35 detects the P-polarized component. The output (power) of the aiming beam is thus detected, i.e., monitored.

A safety shutter 10 is removed from an optical path by driving of an inserting/removing unit 61 to allow each beam to travel along the optical path and, alternatively, is inserted in the optical path to intercept each beam. The opening and closing of the shutter 10 is detected by a shutter sensor 10a.

A condensing lens 18 condenses each beam onto an entrance end face of the fiber 2, thereby allowing each beam to enter the fiber 2. Each beam delivered into the slit lamp delivery 4 through the fiber 2 is then irradiated to the affected part of the patient's eye through the irradiation part 5.

Figure 3:
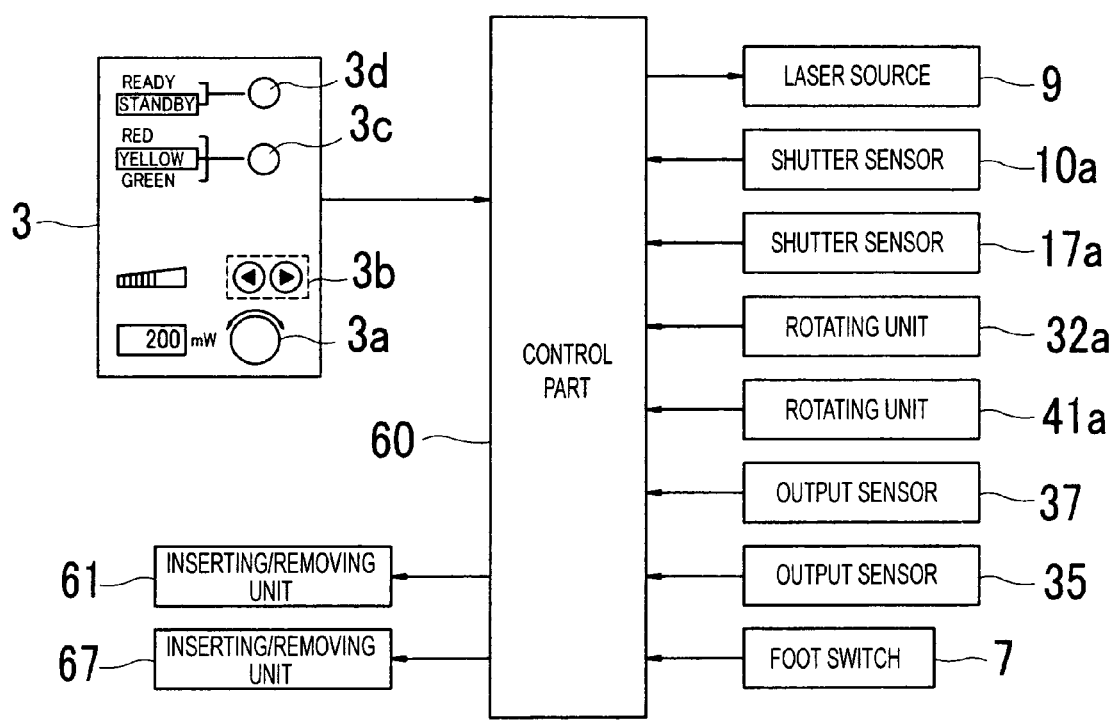
FIG. 3 is a schematic block diagram of a control system of the apparatus.

As shown in FIG. 3, the control box 3, the footswitch 7, the laser source 9, the rotating units 32a and 41a, the output sensors 37 and 35, the inserting/removing units 61 and 67, the shutter sensors 10a and 17a, and others are connected to a control part 60. The control box 3 is provided with a rotary knob 3a for setting an irradiation amount of the treatment beam, a switch 3b for setting an irradiation amount of the aiming beam, a switch 3c for selecting a wavelength (a color) of the treatment beam, and a switch 3d for selecting the operation mode of the apparatus, a READY mode or a STANDBY mode. In addition, the control box 3 is provided with various switches, which are not shown in FIG. 3, for setting irradiation conditions of the treatment beam, e.g., irradiation time (duration), irradiation time interval, and others.

The operation of the apparatus having the above structure will be explained below. The operator operates each switch on the control box 3 to set in advance the irradiation conditions of the treatment beam and the aiming beam. When a wavelength of the treatment beam is selected, a beam of the selected wavelength is emitted by the laser source 9 as below. At the time of power-on, i.e., in the STANDBY mode, the shutter 17 has been closed (inserted in the optical path).

Figure 5:
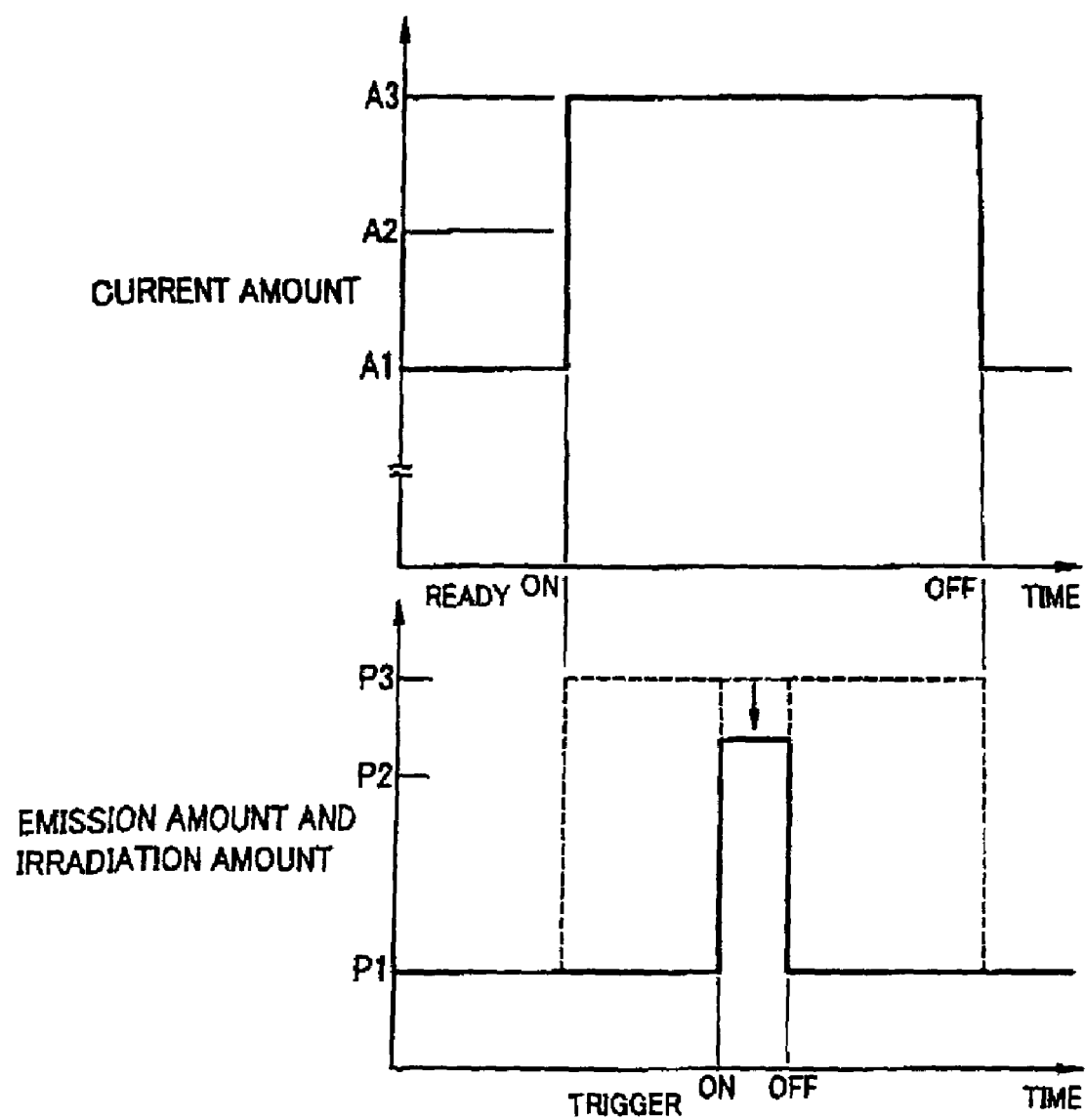
FIG. 5 is a graph showing a relation between a change in an amount of electric current applied to the laser source and changes in an emission amount of a beam and an irradiation amount of the beam.

When the switch 3b is turned on, bringing about a state that the irradiation amount of the aiming beam is not zero, the control part 60 applies an amount A1 of electric current to the laser source 9 as shown in FIG. 5. This electric current amount A1 corresponds to a maximum irradiation amount of the aiming beam. The electric current amount A1 varies depending on the beam wavelengths; for example, 15A for 532 nm, 15A for 561 nm, and 17A for 669 nm in the present embodiment. When the electric current amount A1 corresponding to the selected beam wavelength is applied to the laser source 9, this laser source 9 emits a beam in an amount P1. This emission amount P1 varies depending on the beam wavelengths; 300 mW for 532 nm, 300 mW for 561 nm, and 500 mW for 659 nm in the present embodiment. Upon turn-on of the switch 3b, the control part 60 drives the inserting/removing unit 61 to open the shutter 10, which is moved out of the optical path.

In the beam emitted by the laser source 9, 0.1% of the P-polarized component reflected by the beam splitter 11 is adjusted as the aiming beam in the irradiation amount suet by the switch 3b. Specifically, the control part 60 rotates the polarizing member 41 through the rotating unit 41a to attenuate the amount of the P-polarized component to be allowed to pass through the polarizing member 41, thereby changing the amount of the aiming beam which enters the fiber 2. Through the fiber 2, the aiming beam is delivered into the irradiation part 5 of the slit lamp delivery 4.

By observing the fundus of the patient's eye and the irradiated aiming beam through the slit lamp delivery 4, the operator makes alignment of the aiming beam with respect to the affected part. Then, the operator depresses the switch 3d to switch the operation mode of the apparatus from the STANDBY mode to the READY mode in which irradiation of the treatment beam is enabled. When switched to the READY mode, the control part 60 controls in plural levels the amount of electric current to be applied to the laser source 9, as shown in FIGS. 5 and 6, according to the irradiation amount of the treatment beam set by the knob 3a.

For instance, when the irradiation amount of the treatment beam is set at an amount for which the emission amount of the beam by the laser source 9 is required to be 900 mW or more, the control part 60 supplies an amount A3 of electric current to the laser source 9. This electric current amount A3 varies depending on the beam wavelengths; for example, 20A for 532 nm, 26A for 561 nm, and 25A for 669 nm in the present embodiment. When the electric current amount A3 corresponding to the selected beam wavelength is applied to the laser source 9, this laser source 9 emits a beam in an amount P3, which is 3500 mW for 532 nm, 1200 mW for 561 nm, and 1200 mW for 659 nm in the present embodiment. In the beam emitted by the laser source 9, 99.9% of the P-polarized component having passed through the beam splitter 11 is adjusted as the treatment beam in the irradiation amount set by the knob 3a. Specifically, the control part 60 rotates the ½ wave member 32 through the rotating unit 32a to change the amount of the S-polarized component to be reflected by the beam splitter 15, thereby changing the amount of the treatment beam.

Figure 6:
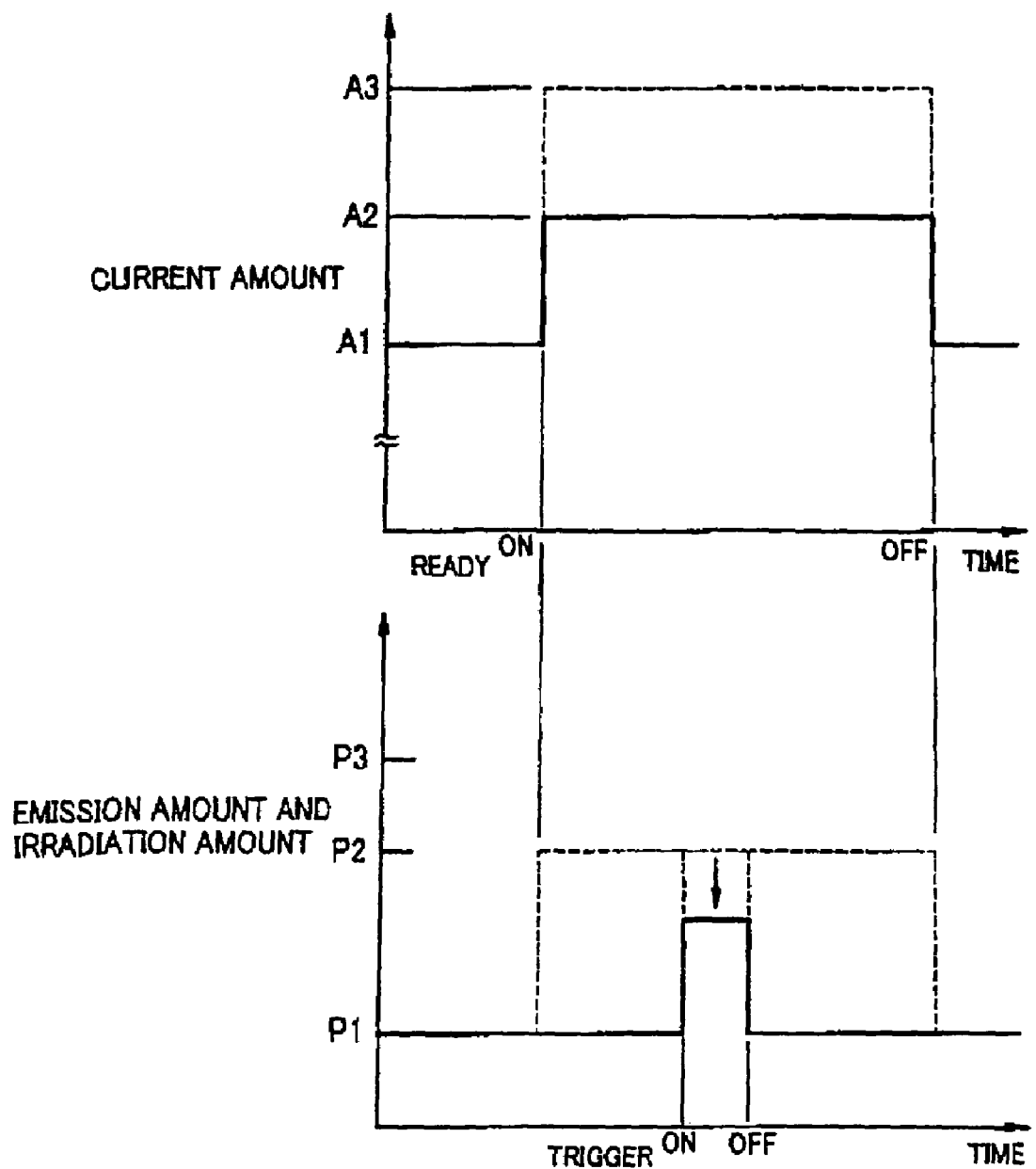
FIG. 6 is a graph showing another relation between a change in an amount of electric current applied to the laser source and changes in an emission amount of a beam and an irradiation amount of the beam.

When the irradiation amount is set at an amount which enables irradiation even where the emission amount of the beam by the laser source 9 is less than 900 mW, the control part 60 supplies an amount A2 of electric current to the laser source 9, as shown in FIG. 6. This electric current amount A2 varies depending on beam wavelengths; for example, 17A for 532 nm, 20A for 561 nm, and 20A for 659 am in the present embodiment. Upon application of the electric current amount A2 corresponding to the selected beam wavelength to the laser source 9, this laser source 9 emits a beam in an amount P2, which is 900 mW for every wavelength in the present embodiment. Then, the control part 60 rotates the ½ wave member 32 through the rotating unit 32a to change the amount of the S-polarized component to, be reflected by the beam splitter 15, thereby changing the amount of the treatment beam.

It is to be noted that the amount P1 corresponds to a first emission amount in claim 2 of the invention and the amounts P2 and P3 correspond to a second emission amount in claim 2; and the amount P2 also corresponds to a first emission amount in claim 3 and the amount P3 corresponds to a second emission amount in claim 3.

Even in the READY mode, the beam is adjusted as the aiming beam in the irradiation amount set by the switch 3b. Specifically, the emission amount by the laser source 9 is determined differently between the READY mode and the STANDBY mode, depending on the set irradiation amount of the treatment beam. Accordingly, the control part 60 controls an available range of the rotation angle of the polarizing member 41 to be rotated by the rotating unit 41a according to the amount of electric current applied to the laser source 9, thereby providing the aiming beam in the irradiation amount set by the switch 3b.

Figure 7A:
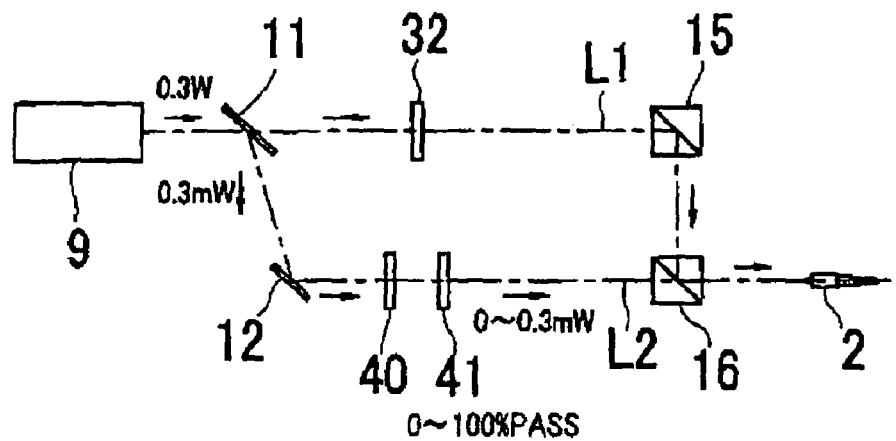
FIGS. 7A-7C are views showing relations between an emission amount of a beam by the laser source and a change in an irradiation amount of an aiming beam.
Figure 9:
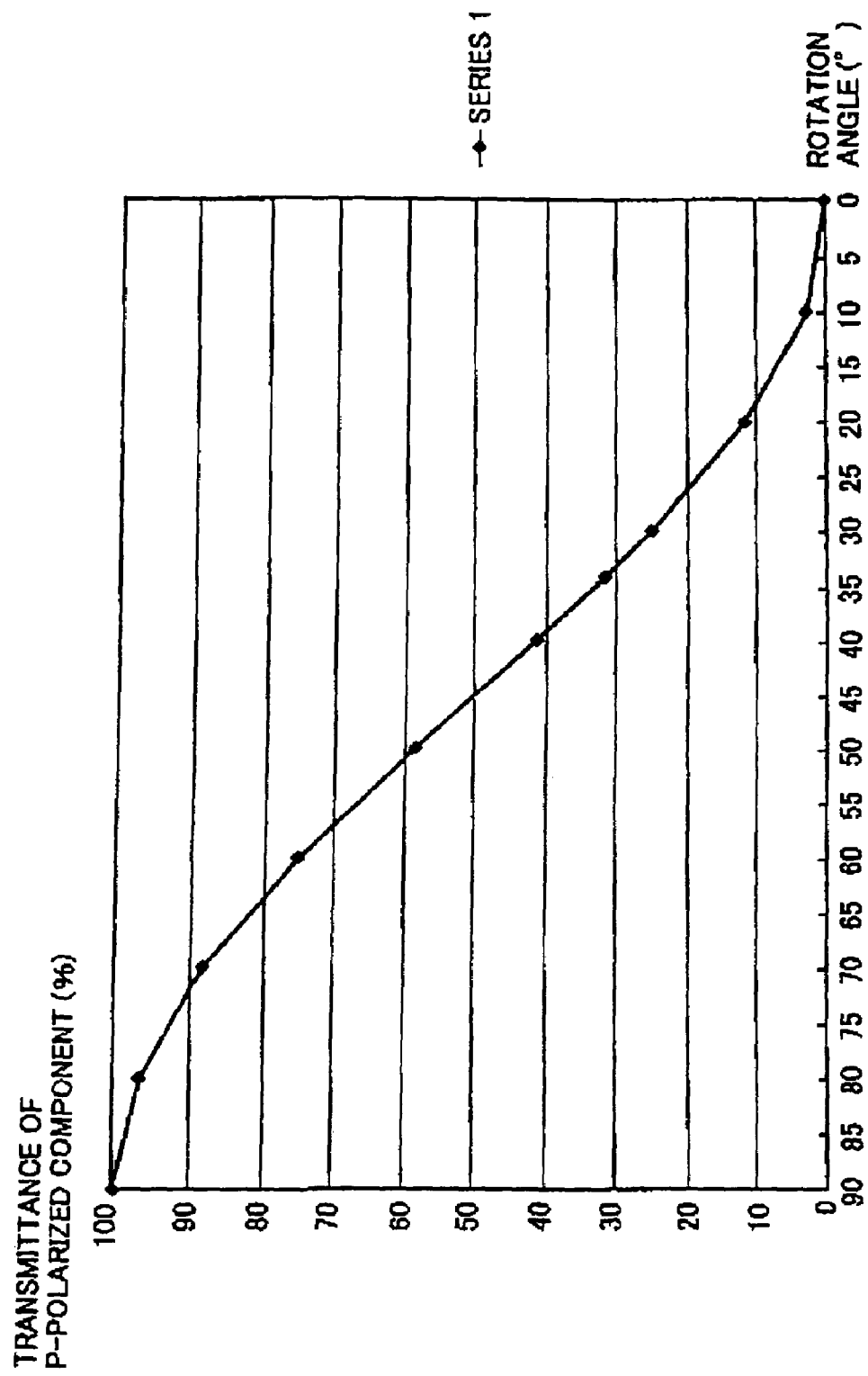
FIG. 9 is a graph showing a relation between a rotation angle of a polarizing member and transmittance of a P-polarized component.

As shown in FIG. 7A, in the STANDBY mode in which a wavelength of 561 nm is selected, the laser source 9 emits a beam in the amount P1 (300 mW), and 0.3 mW of the P-polarized component enters the polarizing member 41. For instance, assume that the polarizing member 41 at a rotation angle of 90° allows 100% of the P-polarized component to pass through it and the polarizing member 41 at a rotation angle of 0° allows 0% of the P-polarized component to pass through it (see FIG. 9). When the rotation angle of the polarizing member 41 is controlled in a range of 0° to 90°, the irradiation amount of the aiming beam can be changed in a range of 0 to 0.3 mW based on the set amount.

Figure 7B:
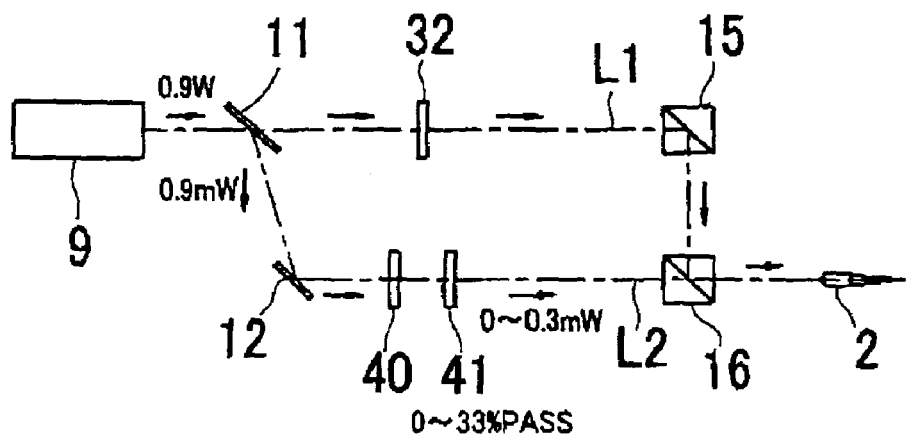

As shown in FIG. 7B, further, in the READY mode in which the irradiation amount is set at an amount which enables irradiation even where the emission amount of the beam by the laser source 9 is less than 900 mW and a wavelength of 561 nm is selected, the laser source 9 emits a beam in the amount P2 (900 mW), and 0.9 mW of the P-polarized component enters the polarizing member 41. When the rotation angle of the polarizing member 41 is controlled in a range of 0° to 34°, the irradiation amount of the aiming beam can be changed in a range of 0 to 0.3 mW (⅓ of 09. mW) based on the set amount.

Figure 7C:
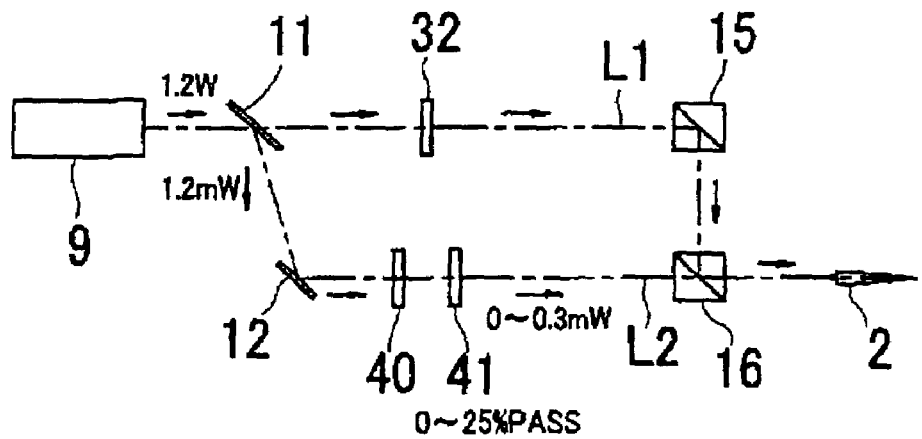
Figure 8:
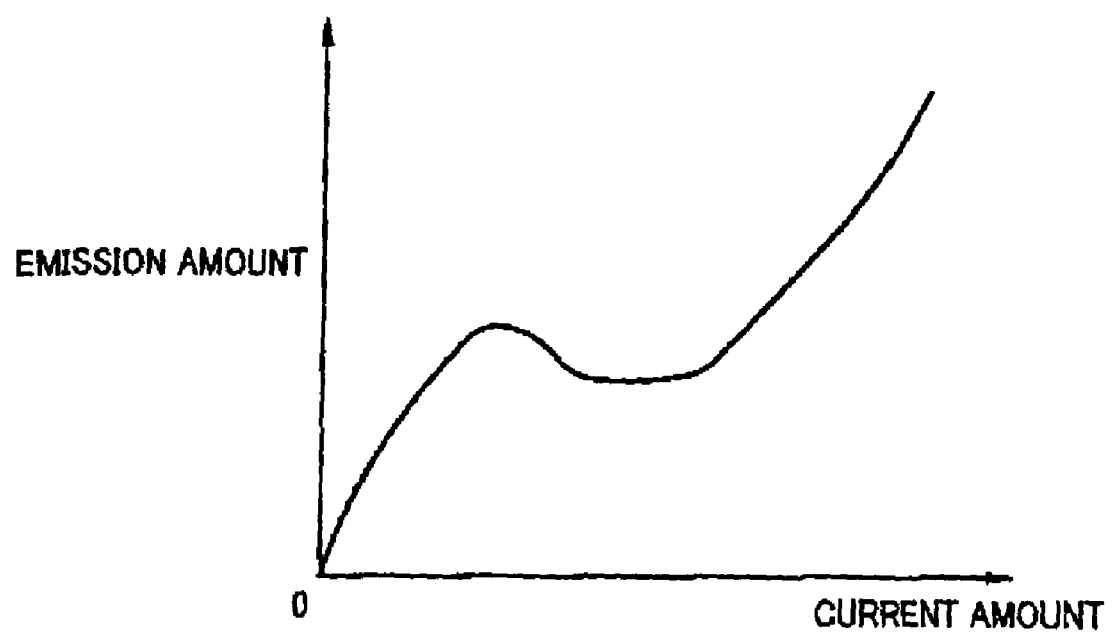
FIG. 8 is a view showing a relation between a change in an amount of electric current applied to a laser source and a change in an emission amount of a beam.

As shown in FIG. 7C) in the READY mode in which the irradiation amount is set at an amount for which the emission amount of the beam by the laser source 9 is required to be 900 mW or more and a wavelength of 561 nm is selected, the laser source 9 emits a beam in the amount P3 (1200 mW), and 1.2 mW of the P-polarized component enters the polarizing member 41. When the rotation angle of the polarizing member 41 is controlled in a range of 0° to 30°, the irradiation amount of the aiming beam can be changed in a range of 0 to 0.3 mW (¼ of 1.2 mW) based on the set amount.

When the operator depresses the footswitch 7, the shutter 17 is opened, which is moved out of the optical path. The shutter 17 is opened only while the footswitch 7 is depressed and the shutter 17 is closed when the footswitch 7 is released. In other words, only during depression of the footswitch 7, the treatment beam is irradiated according to the set irradiation time and other conditions.

As described above, the emission amount of the beam by the laser source 9 is controlled in plural levels according to the set irradiation amount of the treatment beam. This makes it possible to reduce a load on the laser source, thus increasing the, useful life thereof The ophthalmic treatments by incising an iris, cauterizing a ciliary body, or other operations, are made by the treatment beam in an irradiation amount for which the emission amount of the beam by the laser source is required to be 900 mW or more. Other ophthalmic treatments by photocoagulating a fundus, or other operations are made by the treatment beam in another irradiation amount which enables irradiation even where the emission amount of the beam by the laser source is less than 900 mW. Comparing both cases, the apparatus will be used for the photocoagulation treatment at a higher frequency. Accordingly, the frequency of setting the emission amount of the beam by the laser source at a lower value is increased. Thus, the invention will be more effective.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. A laser treatment apparatus for performing treatment by irradiating an affected part with a treatment laser beam, the apparatus comprising:

a laser source that includes a laser rod for generating beams of a plurality of different wavelengths by excitation light and is capable of selectively emitting treatment laser beams of a plurality of different wavelengths by selectively utilizing the generated beams;

a selection unit that selects a treatment laser beam to be used for treatment from among the treatment laser beams of the plurality of different wavelengths by selecting a wavelength;

a first setting unit that sets an irradiation amount of the selected treatment beam to be irradiated onto the affected part;

an emission amount changing unit that changes an emission amount of the selected treatment beam to be emitted by the laser source in plural levels according to a change in amount of electric current to be applied to the laser source, the emission amount and the change levels thereof according to the electric current amount being different by the wavelength of the selected treatment beam;

an optical system including an attenuating unit that gradually attenuates the selected treatment beam emitted by the laser source; and a control part that controls the emission amount changing unit and the attenuating unit based on the irradiation amount of the selected treatment beam set by the first setting unit, wherein the control part controls the emission amount changing unit and the attenuating unit to change the emission amount of the selected treatment beam to a first emission amount and attenuate the first emission amount of the emitted treatment beam to the set irradiation amount when the set irradiation amount of the selected treatment beam is less than a reference value and to change the emission amount of the selected treatment beam to a second emission amount and attenuate the second emission amount of the emitted treatment beam to the set irradiation amount when the set irradiation amount of the selected treatment beam is the reference value or more, the second emission amount being larger than the first emission amount.

2. The laser treatment apparatus according to claim 1, further comprising a second setting unit that sets an irradiation amount of an aiming laser beam, wherein the control part controls the attenuating unit based on the set irradiation amount of the aiming beam and the emission amount of the selected treatment beam according to the set irradiation amount of the selected treatment beam.

3. The laser treatment apparatus according to claim 2, further comprising a beam splitter that splits the selected treatment beam emitted by the laser source at a predetermined ratio, wherein the attenuating unit includes a first attenuating unit for the treatment beam and a second attenuating unit for the aiming beam, the attenuating units being disposed in respective optical paths of split beams.

4. The laser treatment apparatus according to claim 1, wherein the laser source includes a solid-state laser medium and a wavelength converter and is capable of emitting the treatment beams of the plurality of different wavelengths in a visible region.

* * * * *